United States Patent
Kelly et al.

(10) Patent No.: US 7,455,671 B2
(45) Date of Patent: *Nov. 25, 2008

(54) SURFACE ELECTRODE MULTIPLE MODE OPERATION

(75) Inventors: Amy C. Kelly, San Francisco, CA (US); Steven K. Landreville, Mountain View, CA (US); Robert J. Garabedian, Tyngsboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/867,668

(22) Filed: Oct. 4, 2007

(65) Prior Publication Data

US 2008/0027426 A1    Jan. 31, 2008

Related U.S. Application Data

(63) Continuation of application No. 11/144,848, filed on Jun. 3, 2005, now Pat. No. 7,278,993, which is a continuation of application No. 10/388,143, filed on Mar. 13, 2003, now Pat. No. 6,918,907.

(51) Int. Cl.
    *A61B 18/14* (2006.01)
(52) U.S. Cl. .......................................... 606/41; 607/99
(58) Field of Classification Search .................... 606/41
    See application file for complete search history.

(56) References Cited

U.S. PATENT DOCUMENTS

| 5,279,569 | A | 1/1994 | Neer et al. |
| 6,190,383 | B1 | 2/2001 | Schmaltz et al. |
| 6,379,353 | B1 | 4/2002 | Nichols |
| 6,470,218 | B1 | 10/2002 | Behl |
| 6,918,907 | B2 * | 7/2005 | Kelly et al. .................. 606/41 |
| 2002/0111615 | A1 | 8/2002 | Cosman et al. |
| 2002/0120260 | A1 | 8/2002 | Morris et al. |
| 2002/0120261 | A1 | 8/2002 | Morris et al. |
| 2002/0120263 | A1 | 8/2002 | Brown et al. |
| 2003/0040743 | A1 | 2/2003 | Cosman et al. |

FOREIGN PATENT DOCUMENTS

EP        1 262 156        12/2002

OTHER PUBLICATIONS

PCT International Search Report for PCT/US04/005547, Applicant: Scimed Life Systems, Inc., Forms PCT/ISA/210 and 220, dated Aug. 5, 2004 (7 pages).
PCT Written Opinion of the International Search Authority for PCT/US04/005547, Applicant: Scimed Life Systems, Inc., Form PCT/ISA/237, dated Aug. 5, 2004 (4 pages).

* cited by examiner

*Primary Examiner*—Lee S Cohen
(74) *Attorney, Agent, or Firm*—Vista IP Law Group LLP

(57) ABSTRACT

A surface electrode for ablating tissue is provided. The surface electrode comprises a base, a plurality of tissue penetrating needle electrodes extending from the surface of the base an adjustable distance, and an electrical interface coupled to the plurality of needle electrodes. The adjustability of the needle electrodes allows the depth that the needle electrodes penetrate through tissue to be adjusted.

24 Claims, 9 Drawing Sheets

SURFACE ELECTRODE MULTIPLE MODE OPERATION

CROSS REFERENCE TO RELATED APPLICATION

This application is a continuation of U.S. application Ser. No. 11/144,848, filed Jun. 3, 2005, (now U.S. Pat. No. 7,278,993) which is a continuation of U.S. application Ser. No. 10/388,143, filed Mar. 13, 2003 (now U.S. Pat. No. 6,918,907) the disclosure of which is hereby incorporated by reference.

FIELD OF THE INVENTION

The field of the invention relates generally to the use of ablation devices for the treatment of tissue, and more particularly, RF ablation devices for the treatment of tumors.

BACKGROUND OF THE INVENTION

The delivery of radio frequency (RF) energy to target regions within tissue is known for a variety of purposes. Of particular interest to the present invention, RF energy may be delivered to diseased regions in target tissue for the purpose of causing tissue necrosis. For example, the liver is a common depository for metastases of many primary cancers, such as cancers of the stomach, bowel, pancreas, kidney, and lung. Electrosurgical probes with deploying electrode arrays have been designed for the treatment and necrosis of tumors in the liver and other solid tissues. See, for example, the LeVeen™ Needle Electrode available from Boston Scientific Corporation, which is constructed generally in accord with U.S. Pat. No. 6,379,353, entitled "Apparatus and Method for Treating Tissue with Multiple Electrodes."

The probes described in U.S. Pat. No. 6,379,353 comprise a number of independent wire electrodes that are deployed into tissue from the distal end of a cannula. The wire electrodes may then be energized in a monopolar or bipolar fashion to heat and necrose tissue within a defined volumetric region of target tissue. Difficulties have arisen in using the multiple electrode arrangements of U.S. Pat. No. 6,379,353 in treating tumors that lay at or near the surface of an organ, such as the liver. Specifically, some of the tips of the electrode array can emerge from the surface after deployment. Such exposure of the needle tips outside the tissue to be treated is disadvantageous in a number of respects. First, the presence of active electrodes outside of the confinement of the organ being treated subjects other tissue structures of the patient as well as the treating personnel to risk of accidental contact with the electrodes. Moreover, the presence of all or portions of particular electrodes outside of the tissue being treated can interfere with proper heating of the tissue and control of the power supply driving the electrodes. While it would be possible to further penetrate the needle electrode into the treated tissue, such placement can damage excessive amounts of healthy tissue.

In response to these adverse results, a device for ablating a tumor at or near the surface of tissue has been developed. Specifically, as illustrated in FIG. 1, an ablation assembly 20 comprises a surface electrode 22 and an electrosurgical probe 24, such as a LeVeen™ electrode, that can be operated in a bipolar mode to ablate the tissue in contact with, and between a needle electrode array 26 mounted to the distal end of the probe 24 and the surface electrode 22. As illustrated, the surface electrode 22 comprises a generally flat or planar disk-shaped plate 28 and a plurality of tissue penetrating electrodes 30 that project perpendicularly from the plate 28. The surface electrode 22 further comprises a central aperture 32 that extends through the plate 28, so that the surface electrode 22 can be threaded over the probe 24 and locked into place about the deployed probe 24. The ablation assembly 20 can then be operated in a monopolar or bipolar mode to ablate the tissue in contact with, and between, the electrode array 26 of the probe 24 and the needles electrodes 30 of the surface electrode 22. Further details regarding these types of ablation devices are disclosed in U.S. Pat. No. 6,470,218, entitled "Apparatus and Method for Treating Tumors Near the Surface of an Organ," which is hereby fully and expressly incorporated herein by reference.

Although the ablation assembly illustrated in FIG. 1 is generally useful in ablating superficially oriented tumors, it cannot be used to efficiently and safely ablate such tumors in all circumstances. For example, if the tumor is quite close to the surface of the tissue, placement of the needle electrodes without exposing any metallic surface can be difficult. Also, it may not be practical to use the probe assembly when the tumors are quite shallow. In this case, the surface electrode may be used by itself. Efficient ablation of the tumor, however, may not be achieved if the tumor has a non-uniform thickness.

There thus is a need to provide improved systems and methods for more efficiently and safely ablating superficially oriented tumors.

SUMMARY OF THE INVENTION

In accordance with a first aspect of the present inventions, a surface electrode for ablating tissue comprises a base, a plurality of tissue penetrating needle electrodes extending from the surface of the base an adjustable distance, and an electrical interface coupled to the plurality of needle electrodes. By way of non-limiting example, the adjustability of the needle electrodes allows the depth that the needle electrodes penetrate through tissue to be adjusted. In the preferred embodiment, the needle electrodes are individually adjustable, so that the depths at which the needle electrodes penetrate the tissue can be varied. All or any portion of the needle electrodes carried by the base can be adjustable.

In one preferred embodiment, the base takes the form of a flat plate, but can take the form of any structure from which needle electrodes can be extended. In the preferred embodiment, the needle electrodes extend perpendicularly from the base, but can extend obliquely from the base as well.

The needle electrodes can be mounted to the base in any variety of manners, so that the distance that the needle electrodes extend from the base can be adjusted. For example, the needle electrodes can be mounted to the surface of the base in a threaded arrangement, such that rotation of each needle electrode in one direction increases the distance that the needle electrode extends from the surface of the base, and rotation of each needle electrode in the other direction decreases the distance that the needle electrode extends from the surface of the base. As another example, the needle electrodes can be mounted to the surface of the base in a sliding arrangement, such that displacement of each needle electrode in a distal direction increases the distance that the needle electrode extends from the surface of the base, and displacement of each needle electrode in a proximal direction decreases the distance that the needle electrode extends from the surface of the base. In this case, the surface electrode may further comprise one or more locking mechanisms (e.g., thumb screws) for fixing displacement of the needle electrodes relative to the surface of the base.

The electrical interface may be configured, such that the ablation energy is delivered to the needle electrodes in the desired manner. For example, the electrical interface may couple the needle electrodes in a monopolar or bipolar arrangement. The electrical interface may optionally be adjustable, so that certain needle electrodes can be selectively activated or combinations of needle electrodes can be selectively placed in a bipolar arrangement with respect to each other.

The surface electrode may optionally comprise insulation to minimize inadvertent ablation of healthy tissue. For example, the surface of the base from which the needle electrodes extend may be electrically insulated. Or the surface electrode may further comprise a plurality of electrically insulating sleeves extending from the surface of the base, wherein the insulating sleeves encompass portions of the respective needle electrodes. The insulating sleeves may be optionally extendable from the surface of the base an adjustable length. By way of non-limiting example, the adjustability of the insulating sleeves allows the depth at which healthy tissue is protected to be adjusted.

One or more of the plurality of needle electrodes can comprise a liquid conveying lumen to carry a medium for cooling, therapeutic, or other purposes. For example, the lumen(s) can be configured to perfuse a medium from, and/or internally convey a medium within, the respective needle electrode(s).

In accordance with a second aspect of the present inventions, a tissue ablation system comprises a surface electrode comprising a base and a plurality of tissue penetrating needle electrodes extending from the surface of the base an adjustable distance, and an ablation source (e.g., a radio frequency generator) coupled to the plurality of needle electrodes. The surface electrode can be configured in the same manner described above.

The tissue ablation system can be operated in a monopolar mode or a bipolar mode. For example, the tissue ablation system can further comprise a dispersive electrode, wherein the radio frequency generator comprises a first pole electrically coupled to the surface electrode and a second pole electrically coupled to the dispersive electrode. As another example, the first pole of the radio frequency generator can be electrically coupled to a first set of the plurality of needle electrodes and the second pole can be electrically coupled to a second set of the plurality of needle electrodes. If any of the needle electrodes is configured to convey a medium, the tissue ablation system can further comprise a source of medium (e.g., a pump) in fluid communication with the lumen of the respective needle electrode.

In an optional embodiment, the tissue ablation system can further comprise a clamping device having first and second opposing arms. In this case, the surface electrode can be mounted to one of the arms, and a similar surface electrode can be mounted to the other of the arms. The tissue ablation system can be operated in a bipolar mode by connecting the first pole of the radio frequency generator to the first surface electrode and the second pole to the second surface electrode. Alternatively, a second surface electrode is not provided, but rather a support member with or without tissue penetrating needles. In this case, the support member is used merely to stabilize contact between the surface electrode and the tissue.

In accordance with a third aspect of the present inventions, a method of ablating tissue using a surface electrode with a plurality of needle electrodes is provided. The method comprises adjusting distances that the needle electrodes extend from a base of the surface electrode, penetrating the tissue with the needle electrodes, and conveying ablation energy from the needle electrodes into the tissue (e.g., in a monopolar or bipolar mode) to create a lesion on the tissue. The needle electrode distances can be adjusted prior to, and/or subsequent to, penetrating the tissue with the needle electrodes. Optionally, the needle electrodes from which the ablation energy is conveyed can be dynamically selected.

In the preferred method, the needle electrode distances are individually adjusted, in which case, the needle electrode distances may differ from each other. These needle electrode distances can be adjusted in a variety of manners, e.g., by rotating the needle electrodes or longitudinally sliding the needle electrodes relative to the base.

In order to, e.g., protect healthy tissue, the surface electrode can be insulated by insulating the base and/or insulating portions of the needle electrodes that would otherwise be in contact with the tissue, e.g., by insulating the needle electrode portions with insulation sleeves that extend from the surface of the base. In this case, the distances from which the insulation sleeves extend from the surface of the base can be adjusted.

The method optionally comprises conveying a medium through one or more of the plurality of needle electrodes. For example, the medium can be perfused from the needle electrode(s) into the tissue (e.g., to cool the tissue and/or deliver a therapeutic agent to the tissue) and/or internally conveyed within the needle electrode(s) to cool the needle electrode(s).

In another optional method, the tissue can be penetrated with a plurality of needle electrodes of another surface electrode opposite the needle electrodes of the first surface electrode, in which case, the ablation energy may be conveyed from the other needle electrodes into the tissue. If RF energy is used as the ablation energy, the ablation energy can be conveyed between the first and second surface electrodes. In addition, the needle electrode distances of the second surface electrode can be adjusted in the same manner as the needle electrode distances of the first surface electrode.

BRIEF DESCRIPTION OF THE DRAWINGS

The drawings illustrate the design and utility of a preferred embodiment of the present invention, in which similar elements are referred to by common reference numerals. In order to better appreciate the advantages and objects of the present invention, reference should be made to the accompanying drawings that illustrate this preferred embodiment. However, the drawings depict only one embodiment of the invention, and should not be taken as limiting its scope. With this caveat, the invention will be described and explained with additional specificity and detail through the use of the accompanying drawings in which.

DETAILED DESCRIPTION OF THE PREFERRED EMBODIMENTS

Figure 1:
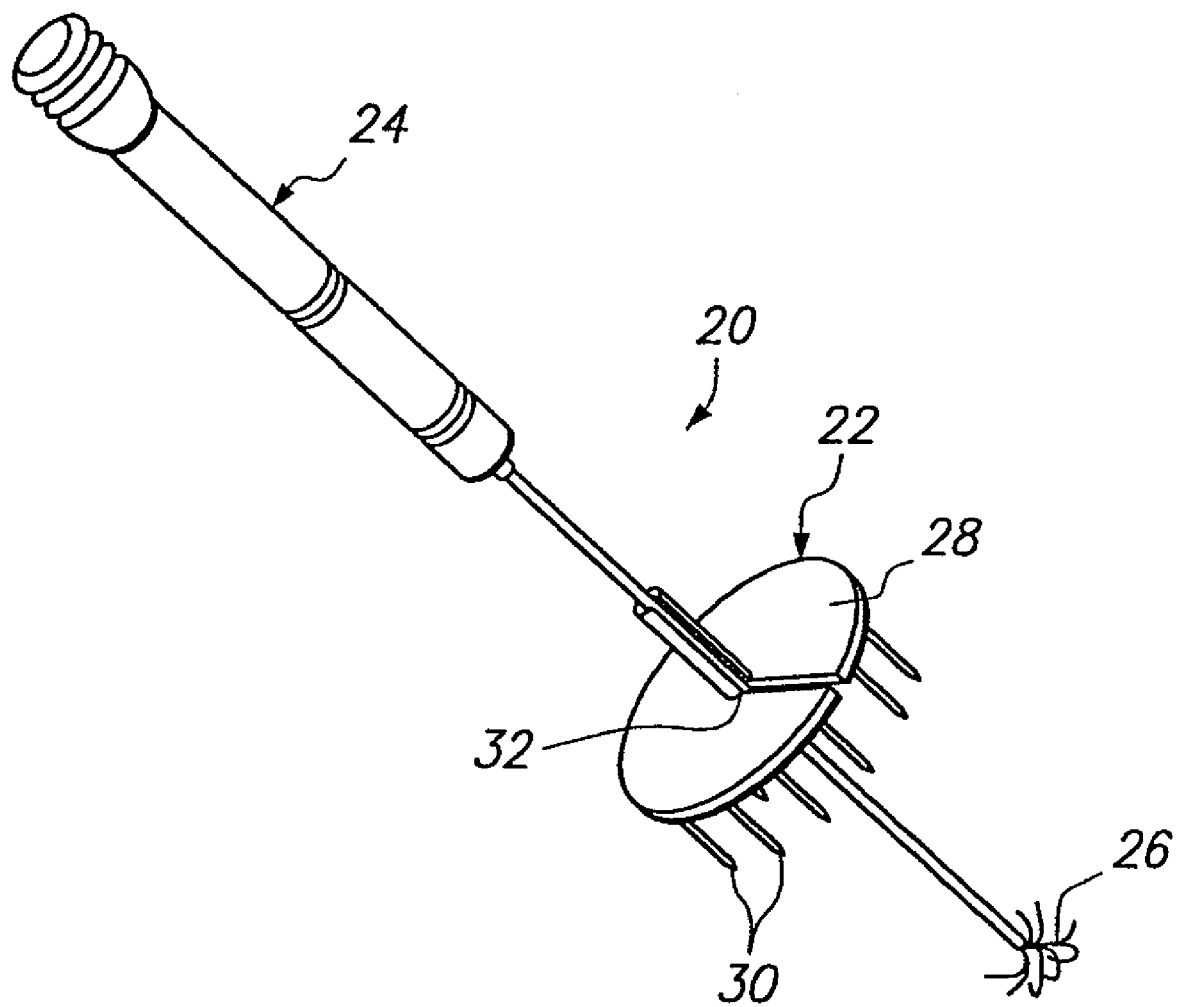
FIG. 1 is a perspective view of a prior art ablation assembly.
Figure 2:
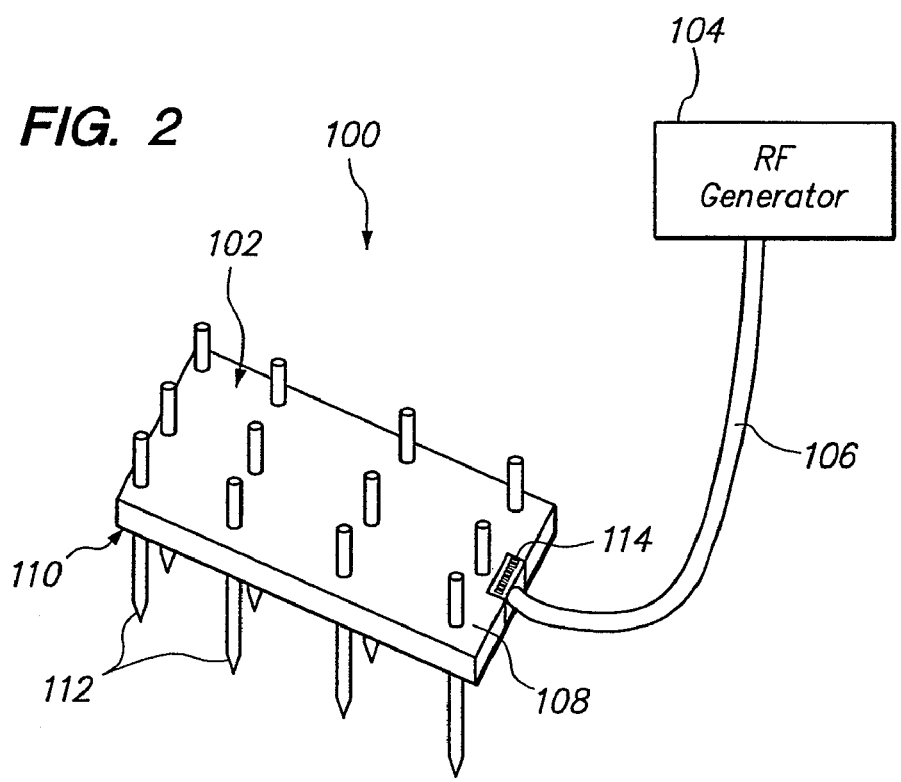
FIG. 2 is plan view of a tissue ablation system constructed in accordance with one preferred embodiment of the present inventions.

FIG. 2 illustrates a tissue ablation system 100 constructed in accordance with a referred embodiment of the present invention. The tissue ablation system 100 generally comprises a surface electrode 102, which is configured to be applied to the surface of tissue, e.g., an organ, in order to ablate target tissue therein, and a radio frequency (RF) generator 104 configured for supplying RF energy to the surface electrode 102 via a cable 106 in a controlled manner. In the embodiment illustrated in FIG. 2, only one surface electrode 102 is shown. As will be described in further detail below, however, multiple surface electrodes 102 can be connected to the RF generator 104 depending upon the specific ablation procedure that the physician selects.

Figure 3:
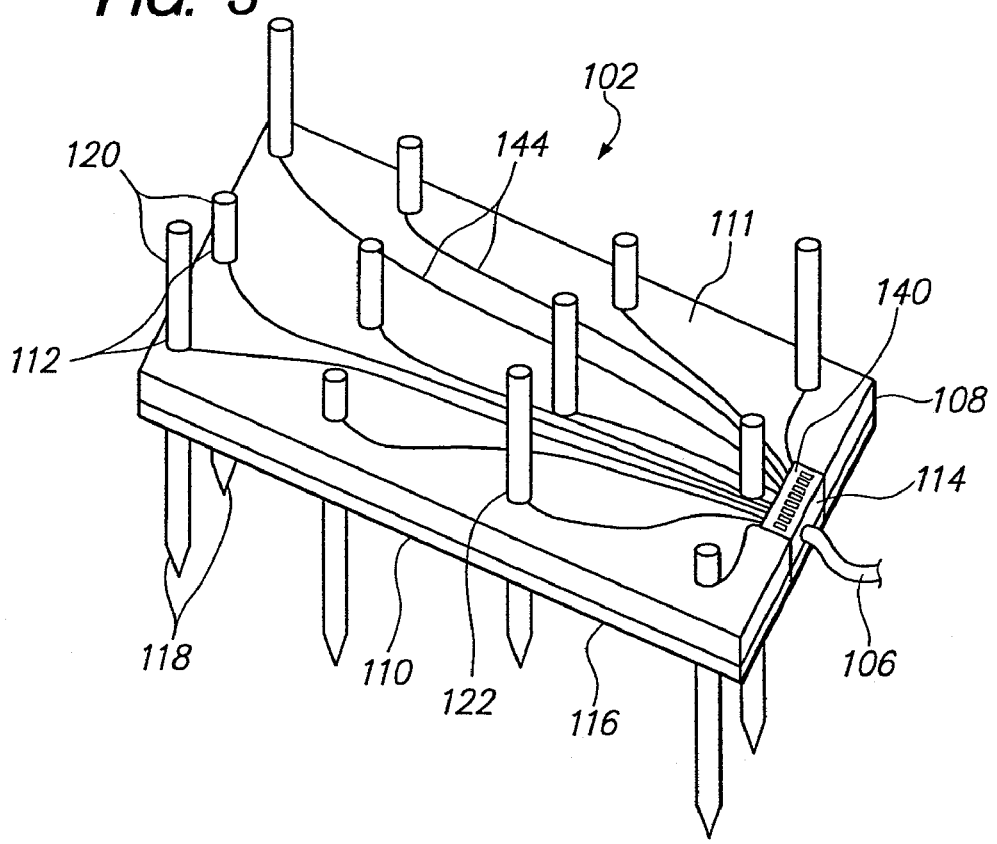
FIG. 3 is a perspective view of one preferred embodiment of a surface electrode that can be used in the tissue ablation system of FIG. 2, wherein an electrical interface that can configure the needle electrodes in a monopolar arrangement is particularly shown.

Referring further to FIG. 3, the surface electrode 102 generally comprises a base 108 having a flat surface 110, an array of needle electrodes 112 extending from the surface 110 of the base 108, and an electrical interface 114 for electrically coupling the needle electrodes 112 to the RF generator 104.

In the illustrated embodiment, the base 108 takes the form of a flat rectangular plate, but other shapes (e.g., circular, oval, quadrangular) can be used, depending upon the nature of the tissue to be ablated. Exemplary bases will have a length in the range of 10 mm to 100 mm, preferably from 30 mm to 60 mm, a width in the range of 10 mm to 100 mm, preferably from 30 mm to 60 mm, and a thickness in the range of 1 mm to 20 mm, preferably from 5 mm to 15 mm. Preferably, the base 108 is composed of a rigid material, such as, e.g., Acrylonitrile Butadiene Styrene (ABS), polycarbonate, polyvinylchloride (PVC), aluminum, or stainless steel. In this manner, application of force on any flat portion of the base 108 will uniformly distribute the force along the surface 110 of the base 108, so that all of the needle electrodes 112 will penetrate the tissue. In alternative embodiments, however, the base 108 may be composed of a semi-rigid or flexible material. In this manner, the base 108 can be conveniently conformed to the curved surface of tissue. In this case, the force needed to penetrate the tissue with the needle electrodes 112 can be applied to the base 108 in a uniformly distributed manner, e.g., using the entire palm of a hand, or can be serially applied to portions of the base 108 so that the needle electrodes 112 penetrate the tissue in a piece-meal fashion.

In any event, if the base 108 is composed of an electrically conductive material, a layer of insulation 116, e.g., rubber, is disposed on the surface 110 of the base 108 using suitable means, such as bonding. In this manner, any ablation energy will be concentrated within the needle electrodes 112, so that only the target tissue is ablated, thereby preventing non-target tissue, e.g., the surface of the tissue in contact with the surface 110 of the base 108, from being ablated.

The needle electrodes 112 are composed of a rigid electrically conductive material, e.g., stainless steel. The needle electrodes 112 preferably have circular cross-sections, but may have non-circular cross-sections, e.g., rectilinear cross-sections. Exemplary needle electrodes will have a diameter in the range of 0.6 mm to 3.4 mm, preferably from 1.1 mm to 1.6 mm, and a length in the range of 10 mm to 70 mm, preferably from 20 mm to 50 mm. The distal ends of the needle electrodes 112 may be honed or sharpened to facilitate their ability to penetrate tissue. The distal ends 118 of these needle electrodes 112 may be hardened using conventional heat treatment or other metallurgical processes. The needle electrodes 112 are covered with insulation (not shown), although they will be at least partially free from insulation over their distal ends 118. As will be described in further detail below, the portion of the needle electrodes 112 that can be placed in contact with the base 108 are also free of insulation.

In the illustrated embodiment, the RF current is delivered to the needle electrodes 112 in a monopolar fashion. Therefore, the current will pass through the needle electrodes 112 and into the target tissue, thus inducing necrosis in the tissue. To this end, the needle electrodes 112 are configured to concentrate the energy flux in order to have an injurious effect on tissue. However, there is a dispersive electrode (not shown) which is located remotely from the needle electrodes 112, and has a sufficiently large area—typically 130 cm$^2$ for an adult—so that the current density is low and non-injurious to surrounding tissue. In the illustrated embodiment, the dispersive electrode may be attached externally to the patient, using a contact pad placed on the patient's skin.

Alternatively, the RF current is delivered to the needle electrodes 112 in a bipolar fashion, which means that current will pass between "positive" and "negative" electrodes 112. As will be described in further detail below, RF current can also pass between needle electrodes 112 of two or more surface electrodes 102 in a bipolar fashion.

Figure 4:
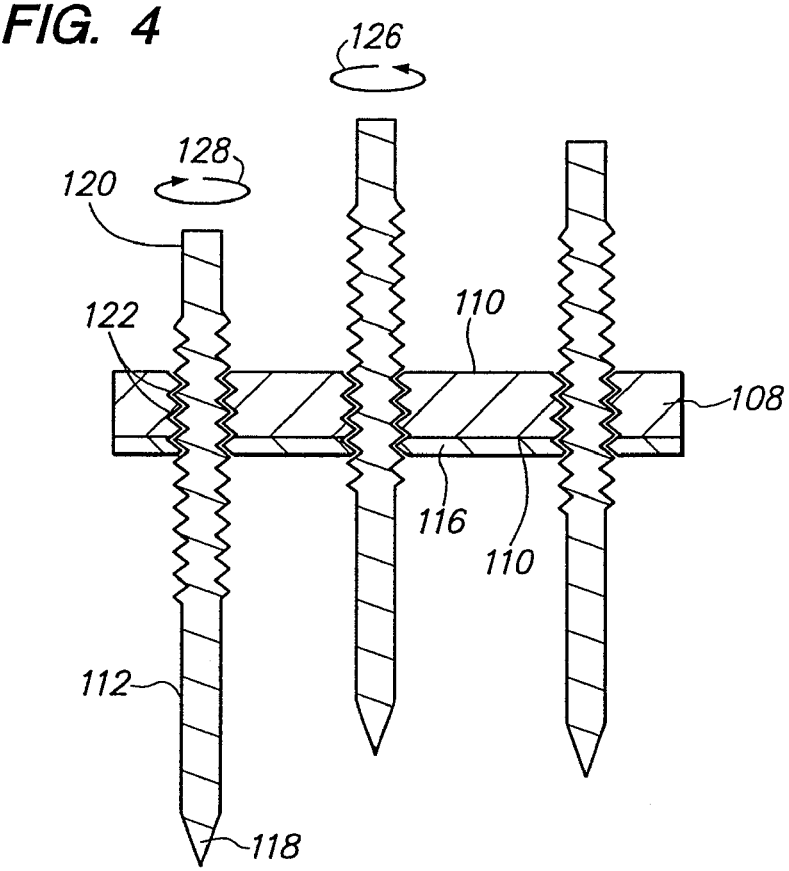
FIG. 4 is a cross-sectional view of the surface electrode of FIG. 3, wherein adjustment of needle electrodes are accomplished using a threaded arrangement.

The lengths of the needle electrodes 112 are adjustable, i.e., the needle electrodes 112 extend from the surface 110 of the base 108 an adjustable distance. Specifically, in the illustrated the proximal ends 120 of the needle electrodes 112 are mounted within apertures 122 formed through the base 108 in a threaded arrangement. As best shown in FIG. 4, the shafts of the needle electrodes 112 and the respective apertures 122 formed through the base 108 include threads 124, such that rotation of the needle electrodes 112 in one direction 126 (here, in the counterclockwise direction) decreases the distances that the needle electrodes 112 extend from the surface 110 of the base 108, and rotation of the needle electrodes 112 in the opposite direction 128 (here, in the clockwise direction) increases the distances that the needle electrodes 112 extend from the surface 110 of the base 108. As can be appreciated, the lengths of the needle electrodes 112 are individually adjustable, so that the distances that the respective needle electrodes 112 extend from the surface 110 of the base 108 may differ, as clearly shown in FIG. 4.

Figure 5:
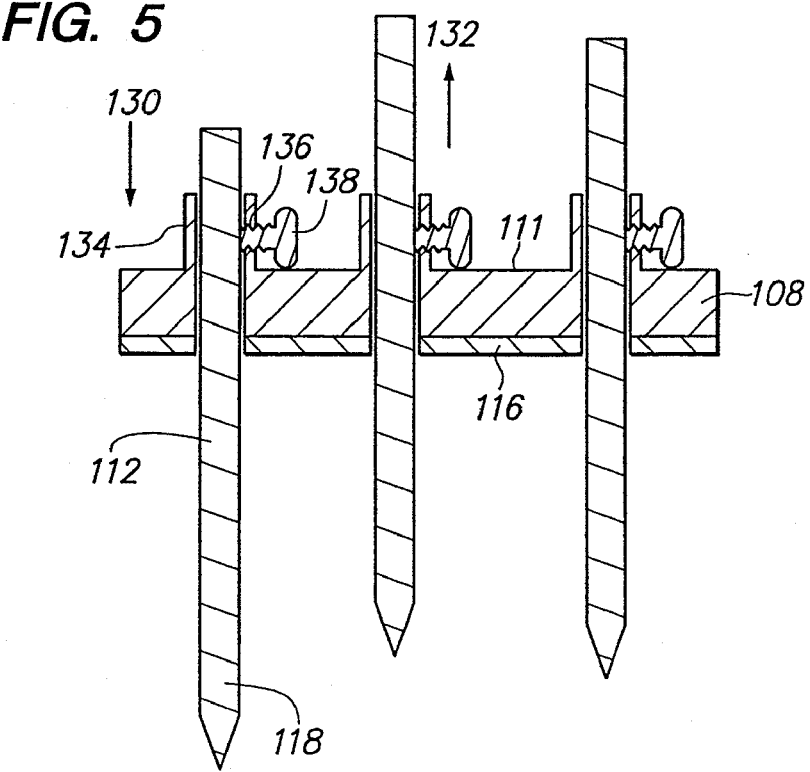
FIG. 5 is a cross-sectional view of the surface electrode of FIG. 3, wherein adjustment of needle electrodes are accomplished using a sliding arrangement.

Alternatively, as illustrated in FIG. 5, the shafts of the needle electrodes 112 can be slidably mounted within the apertures 122 formed through the base 108, so that longitudinal translation of the needle electrodes 112 relative to the apertures 122 in the distal direction 130 increases the distances that the needle electrodes 112 extend from the surface 110 of the base 108, and longitudinal translation of the needle electrodes 112 relative to the apertures 122 in the proximal direction 132 decreases the distances that the needle electrodes 112 extend from the surface 110 of the base 108. In order to fix the needle electrodes 112 relative to the base 108, the base 108 comprises bosses 134 formed along its opposite surface 111. Each of the bosses 134 comprises a threaded hole 136 with an associated thumb screw 138. Thus, the shafts of the needle electrodes 112 can be affixed within the bosses 134 by tightening the thumb screws 138, and released within the bosses 134 by loosening the thumb screws 138.

Referring back to FIG. 3, the electrical interface 114 provides a means for selectively configuring the needle electrodes 112. For example, in a monopolar arrangement where all of the needle electrodes 112 are coupled to a first pole of the RF generator 104 and a separate dispersive electrode (not shown) is coupled to a second pole of the RF generator 104, the electrical interface 114 can comprise a single dip switch 140 coupled to the first pole of the RF generator 104. In this manner, the dip switch 140 can be operated to selectively turn each needle electrode 112 on or off, so that RF energy will be conveyed between some of the needle electrodes 112 and the dispersive electrode, and will not be conveyed between others of the needle electrodes 112 and the dispersive electrode.

Figure 6:
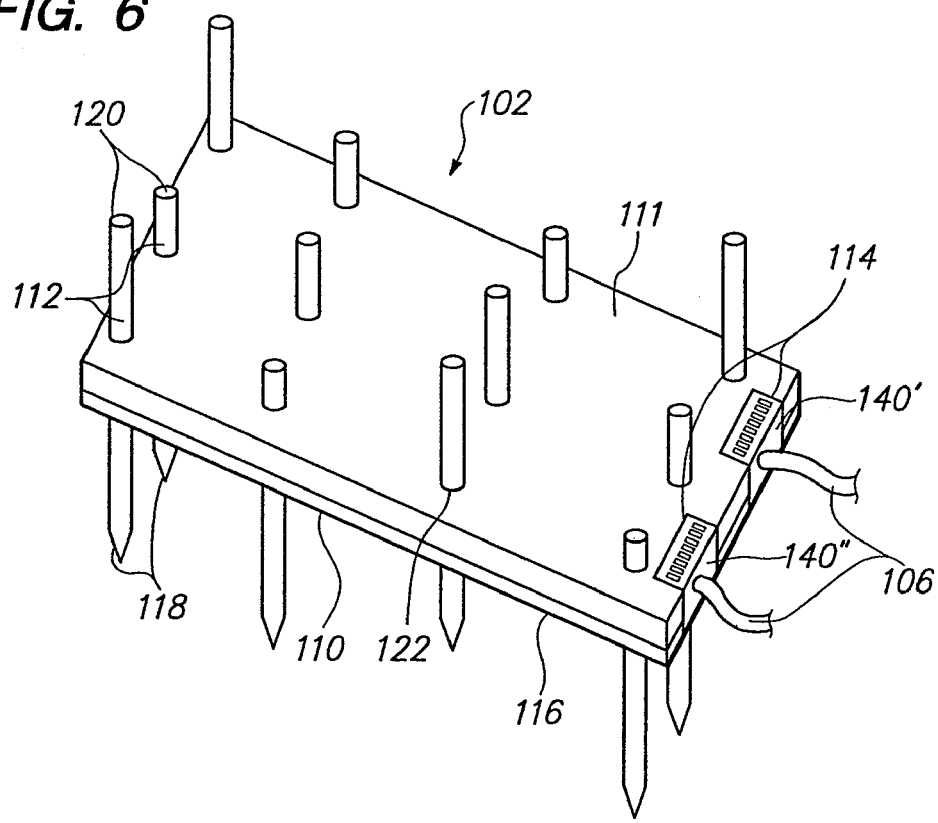
FIG. 6 is a perspective view of another preferred embodiment of a surface electrode that can be used in the tissue ablation system of FIG. 2, wherein an electrical interface that can configure the needle electrodes in a bipolar arrangement is particularly shown.

In a bipolar arrangement where some of the needle electrodes 112 are coupled to the first pole of the RF generator 104 and others of the needle electrodes 112 are coupled to the second pole of the RF generator 104, the electrical interface 114 can take the form of a pair of dip switches 140' and 140" respectively coupled to the two poles of the RF generator 104, as illustrated in FIG. 6. In this manner, the first dip switch 140' can be operated to turn a first subset of needle electrodes 112 on, and the second dip switch 140" can be operated to turn a second different subset of needle electrodes 112 on, so that RF energy will be conveyed between the first and second subsets of needle electrodes 112.

Whether the needle electrodes 112 are operated in a monopolar mode or bipolar mode, the electrical interface 114 is coupled to the respective needle electrodes 112 by electrical paths 144 that are preferably electrically isolated from each other. This can be accomplished depending on the means that is used for adjusting the lengths of the needle electrodes 112. For example, if the lengths of the needle electrodes 112 are adjusted by rotating the needle electrodes 112 within the respective apertures 122, the electrical paths can comprise electrical traces (shown in FIG. 3) that extend along the opposite surface 111 of the base 108 between the electrical interface 114 and the apertures 122 in which the shafts of the needle electrodes 112 are mounted. In this case, the base 108 can be composed of an electrically non-conductive material, in which case, the apertures 122 can be coated with an electrically conductive material, such as, e.g., gold or copper. If the lengths of the needle electrodes 112 are adjusted by longitudinally translating the needle electrodes 112 within the respective apertures 122, the electrical paths 144 can comprise insulated wires (not shown) that extend between the electrical interface 114 and the proximal ends 120 of the needle electrodes 112.

It should be noted, however, that if selective arrangement of the needle electrodes 112 is not desired, and the needle electrodes 112 are not operated in a bipolar mode, the base 108 can be totally composed of an electrically conductive material, in which case, the electrical interface 114 can take the form of a simple connection that operates to couple the cable 106 of the RF generator 104 to the apertures 122 (and thus the needle electrodes) through the base 108 itself.

Figure 7:
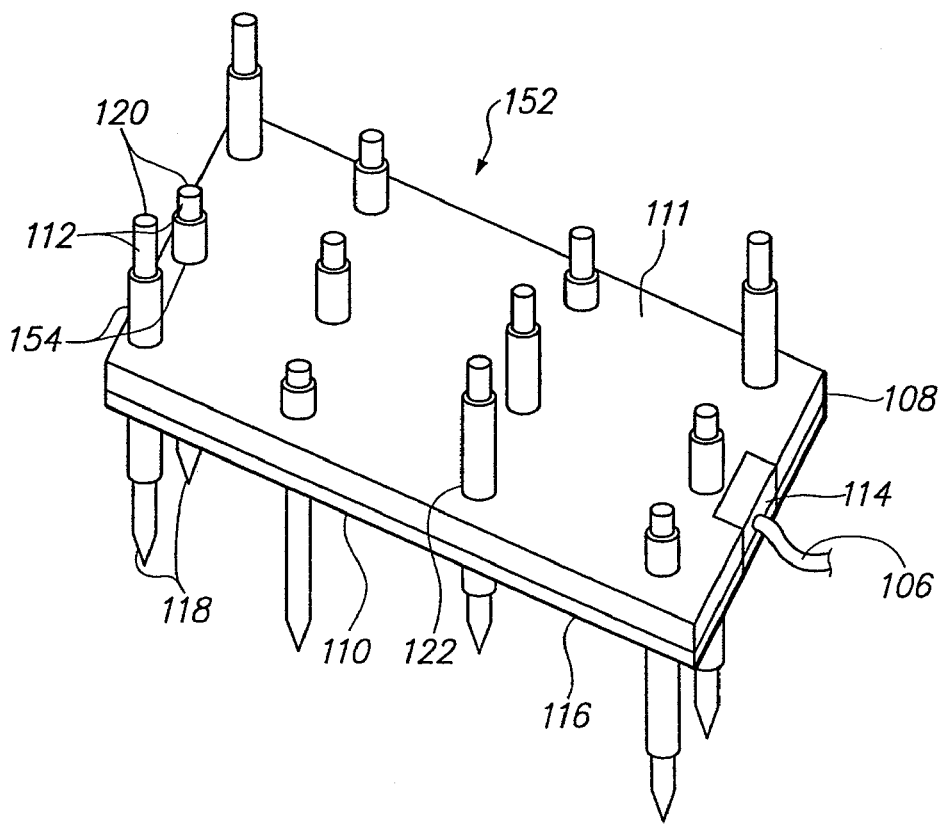
FIG. 7 is a perspective view of a still another preferred embodiment of a surface electrode that can be used in the tissue ablation system of FIG. 2, wherein adjustable insulated sleeves are used to insulate portions of the needle electrodes.

In an optional embodiment of a surface electrode, the electrical insulation associated with the needle electrodes 112 can be adjustable, so that the length of the electrically conductive portion of the needle electrodes 112 that will be in contact with the tissue can be adjusted. For example, as illustrated in FIG. 7, an optional surface electrode 152 is similar to the previously described surface electrode 102, with the exception that it comprises insulating sleeves 154 that are mounted within apertures 122 formed through the base 108.

Figure 8:
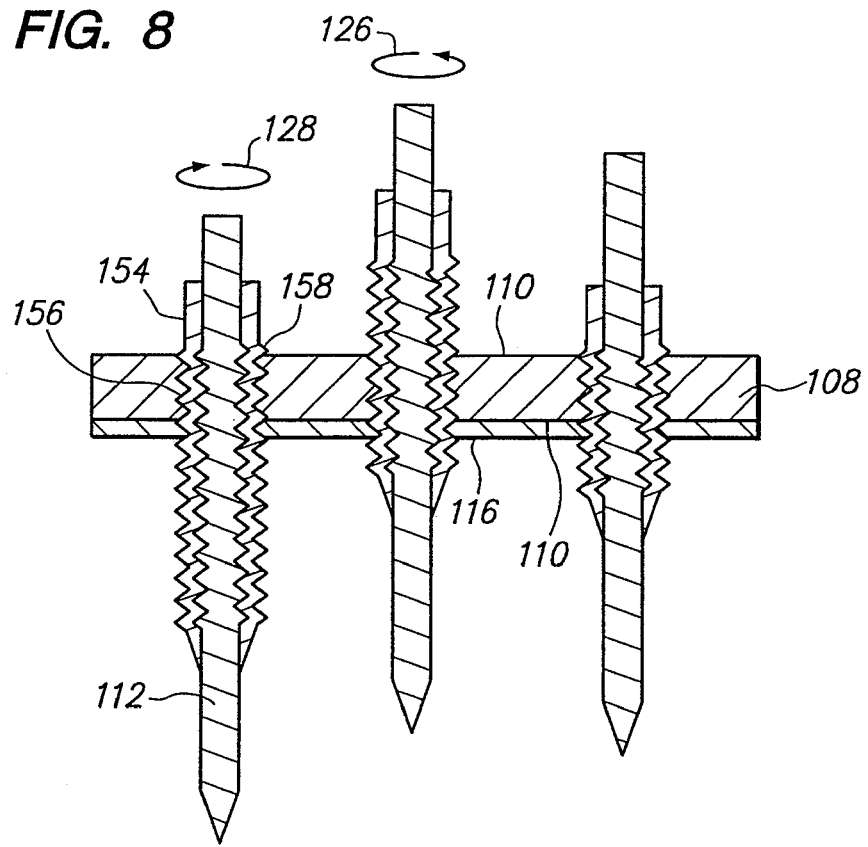
FIG. 8 is a cross-sectional view of the surface electrode of FIG. 7, wherein adjustment of needle electrodes is accomplished using a threaded arrangement.

The lengths of the insulating sleeves 154 are adjustable, i.e., the distances that the insulating sleeves 154 extend from the surface 110 of the base 108 can be varied. Specifically, in the illustrated embodiment, the insulating sleeves 154 are mounted within apertures 122 formed through the base 108 in a threaded arrangement. As best shown in FIG. 8, the insulating sleeves 154 and the respective apertures 122 formed through the base 108 include threads 156, such that rotation of the insulating sleeves 154 in the direction 126 decreases the distances that the insulating sleeves 154 extend from the surface 110 of the base 108, and rotation of the insulating sleeves 154 in the opposite direction 128 increases the distances that the insulating sleeves 154 extend from the surface 110 of the base 108.

As with the previously described surface electrode 102, the lengths of the needle electrodes 112 are also adjustable. In this case, the proximal ends of the needle electrodes 112 are mounted within insulating sleeves 154 in a threaded arrangement. The shafts of the needle electrodes 112 and the insulating sleeves 154 include threads 158, such that rotation of the needle electrodes 112 relative to the insulating sleeves 154 in direction 126 decreases the distances that the needle electrodes 112 extend from the surface 110 of the base 108, and rotation of the needle electrodes 112 relative to the insulating sleeves 154 in the opposite direction 128 increases the distances that the needle electrodes 112 extend from the surface 110 of the base 108.

Figure 9:
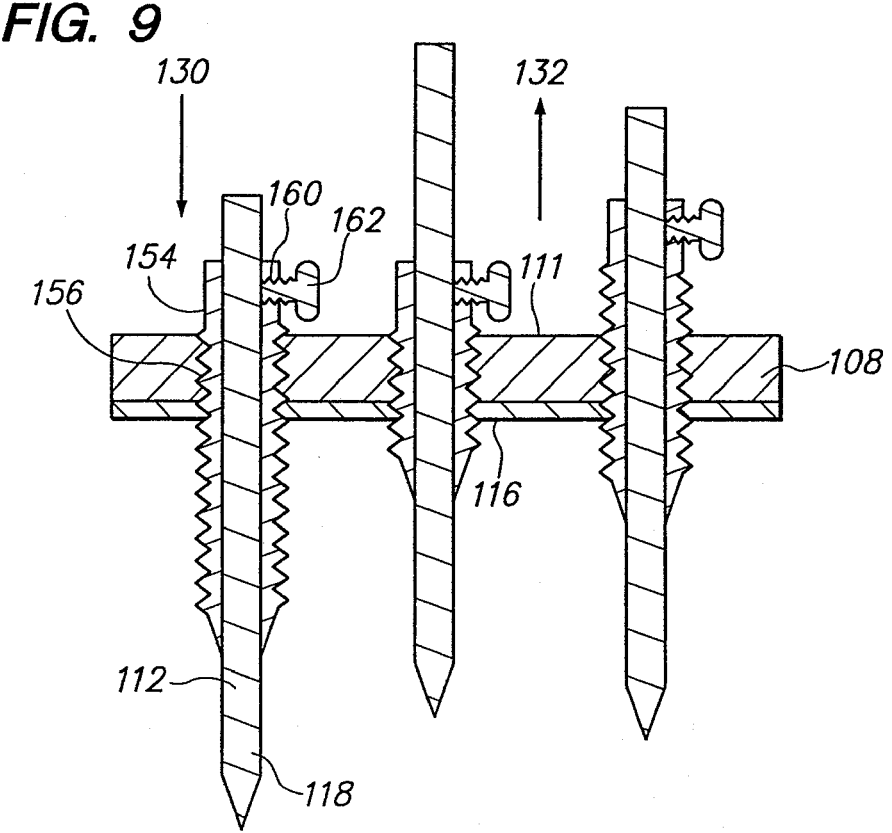
FIG. 9 is a cross-sectional view of the surface electrode of FIG. 7, wherein adjustment of needle electrodes is accomplished using a sliding arrangement.

Alternatively, as illustrated in FIG. 9, the shaft of the needle electrodes 112 can be slidably mounted within the insulating sleeves 154, so that longitudinal translation of the needle electrodes 112 relative to the insulating sleeves 154 in the distal direction 130 increases the distances that the needle electrodes 112 extend from the surface 110 of the base 108, and longitudinal translation of the needle electrodes 112 relative to the insulating sleeves 154 in the proximal direction 132 decreases the distances that the needle electrodes 112 extend from the surface 110 of the base 108. In order to fix the needle electrodes 112 relative to the base 108, each of the insulating sleeves 154 comprises a threaded hole 160 with an associated thumb screw 162. Thus, the shafts of the needle electrodes 112 can be affixed within the insulating sleeves 154 by tightening the thumb screws 162, and released within the insulating sleeves 154 by loosening the thumb screws 162.

Whichever means is used to adjust the needle electrodes 112 within the insulating sleeves 154, the lengths of the insulating sleeves 154 are individually adjustable, so that the distances that the respective insulating sleeves 154 extend from the surface 110 of the base 108, and thus, the lengths of the electrical portions of the needle electrodes 112 that will be in contact with the tissue, may differ. In a similar manner, the needle electrodes 112 are individually adjustable, so that the distances that the respective needle electrodes 112 extend from the surface 110 of the base 108, and thus, the depths that they penetrate tissue, may differ.

The insulating sleeves 154 are composed of a rigid electrically non-conductive material, such as, e.g., fluoropolymer, polyethylene terephthalate (PET), polyetheretherketon (PEEK), polyimide, and other like materials. Alternatively, the insulating sleeves 154 may be composed of an electrically conductive material that is coated within an electrically non-conductive material. If the lengths of the needle electrodes 112 are adjusted by rotating the needle electrodes 112 within the respective apertures 122, the threaded portions of the insulating sleeves 154 are preferably composed of an electrically conductive material to provide an electrical path between the shafts of the needle electrodes 112 and the traces 144 extending along the opposite surface 111 of the base 108. If the lengths of the needle electrodes 112 are adjusted by longitudinally translating the needle electrodes 112 within the insulating sleeves 154, the insulating sleeves 154 can be composed entirely of electrically non-conductive material, since the wires leading from the electrical interface 114 can be coupled directly to the proximal ends 120 of the needle electrodes 112.

Referring back to FIG. 2, as previously noted, the RF generator 104 is electrically connected, via the electrical interface 114, to the needle electrodes 112. The RF generator 104 is a conventional RF power supply that operates at a frequency in the range of 200 KHz to 1.25 MHz, with a conventional sinusoidal or non-sinusoidal wave form. Such power supplies are available from many commercial suppliers, such as Valleylab, Aspen, and Bovie. Most general purpose electro-surgical power supplies, however, operate at higher voltages and powers than would normally be necessary or suitable for controlled tissue ablation.

Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific of San Jose, Calif., which markets these power supplies under the trademarks RF2000™ (100 W) and RF3000™ (200 W).

Having described the structure of the tissue ablation system 100, its operation in treated targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessible via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer assisted tomography (CAT) fluoroscopy, nuclear scanning (using radiolabeled tumor-specific probes), and the like. Preferred is the use of high resolution ultrasound of the tumor or other lesion being treated, either intraoperatively or externally.

Figure 10:
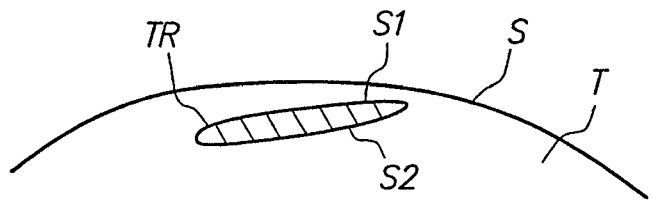
FIGS. 10-13 are plan views illustrating one preferred method of using the tissue ablation system of FIG. 1 to ablate a treatment region within tissue of a patient.
Figure 11:
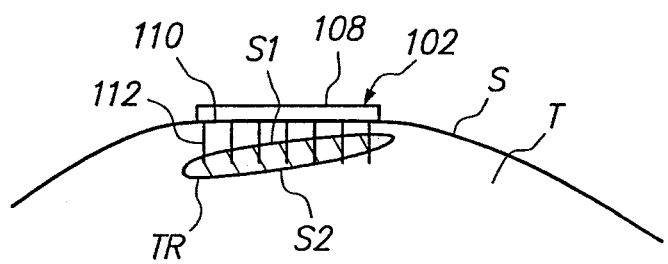
Figure 12:
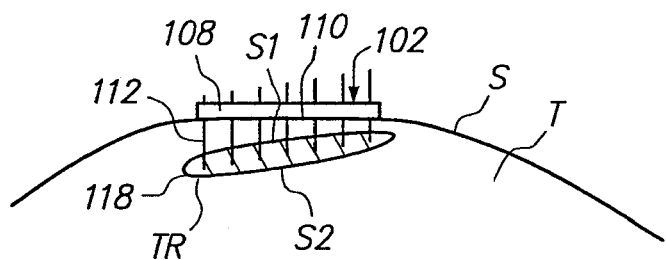

Referring now to FIG. 10-12, the operation of the tissue ablation system 100 is described in treating a treatment region TR, such as a tumor, located below the surface S of tissue T, e.g., an organ. The treatment region TR has a proximal surface S1 and a distal surface S2 opposite the proximal surface S1. As can be seen, the depth of the treatment region TR varies below the surface S of the tissue. Thus, by itself, a surface electrode having needle electrodes with uniform lengths will typically not optimally ablate the treatment region TR. The previously described surface electrode 102, however, can be used to optimally ablate the treatment region TR when properly configured.

First, the electrical interface 114 on the surface electrode 102 is configured, based on the shape of the treatment region TR and whether a monopolar or a bipolar arrangement is desired. The surface electrode 102 is then positioned onto the surface S of the tissue T directly above the treatment region TR, and pressure is applied so that the needle electrodes 112 penetrate into the tissue T, as illustrated in FIG. 11. Preferably, access to the tissue T is gained through a surgical opening made through the skin of the patient. If the surface electrode 102 is small enough or flexible enough, it can alternatively be introduced into contact with the tissue T laparoscopically. Once the needle electrodes 112 are embedded into the tissue T, the distances that the needle electrodes 112 extend from the base 108 of the surface electrode 102 are individually adjusted, so that the distal ends 118 of the needle electrodes 112 penetrate through, or almost penetrate through, the distal surface S2 of the treatment region TR, as illustrated in FIG. 12. As can be appreciated, the deeper a region of the distal surface S2 is below the surface of the tissue T, the greater the distance that the needle electrode 112 associated with that region must extend from the base 108 of the surface electrode 102.

Figure 13:
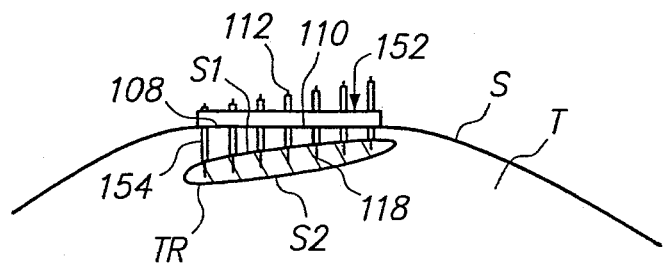

If the surface electrode 152 with adjustable insulating sleeves 154 is used, the distances that the insulating sleeves 154 extend from the base 108 of the surface electrode 102 are individually adjusted, so the distal ends of the insulating sleeves 154 are just above the proximal surface S1 of the treatment region TR, as illustrated in FIG. 13. As can be appreciated, the deeper a region of the proximal surface S1 is below the surface of the tissue T, the greater the distance that the insulating sleeve 204 associated with that region must extend from the base 108 of the surface electrode 102. Thus, as can be seen, the electrically conductive portions of the needle electrodes 112 are only in contact with the treatment region TR.

It should be noted that whichever surface electrode is used, the treatment region TR can be monitored using suitable imaging means to ensure that the needle electrodes 112 and/or insulating sleeves 154 are properly adjusted. It should also be noted that gross adjustments of the needle electrodes 112 and/or insulating sleeves 154 can be accomplished prior to introducing the surface electrode 102 within the patient's body to minimize adjustments to the surface electrode 102 while it is in the patient's body. In this case, fine adjustments of the needle electrodes 112 and/or insulating sleeves 154 can be performed after the needle electrodes 112 have been embedded into the tissue T.

Next, the RF generator 104 is connected to the electrical interface 114 of the surface electrode 102, and then operated to ablate the treatment region TR, resulting in the formation of a lesion that preferably encompasses the entirety of the treatment region TR. If the treatment region TR is substantially larger than that which the surface electrode 102 can cover, thereby resulting in a treatment region TR that is only partially ablated, the surface electrode 102 can be moved to the non-ablated portion of the treatment region TR, and the process can then be repeated. Alternatively, multiple surface electrodes 102 can be used, so that the large treatment region TR can be ablated in one step.

Figure 14:
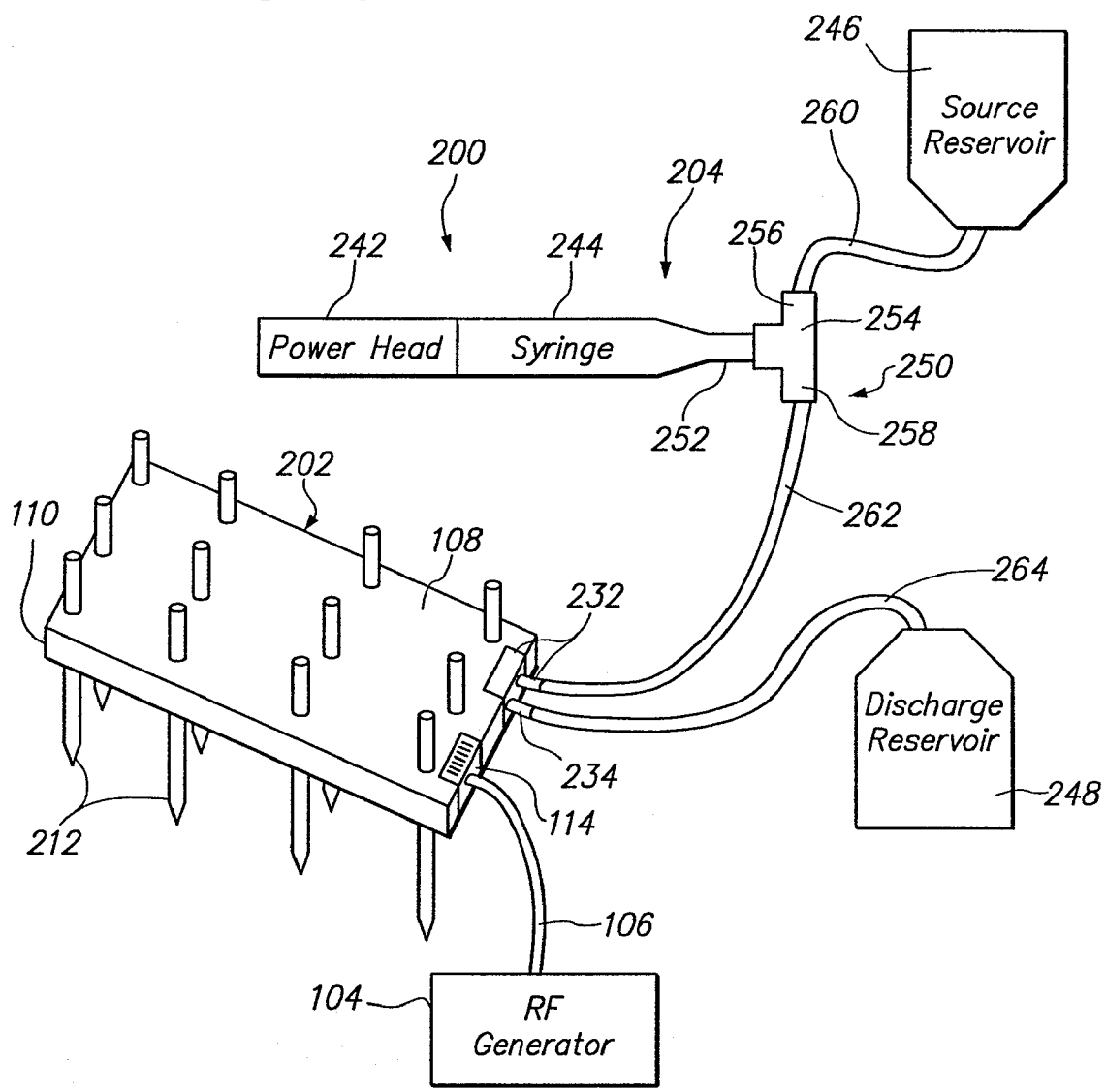
FIG. 14 is plan view of a tissue ablation system constructed in accordance with another preferred embodiment of the present inventions.

FIG. 14 illustrates a tissue ablation system 200 constructed in accordance with another preferred embodiment of the present invention. The tissue ablation system 200 is similar to the previously described tissue ablation system 100, with the exception that it provides cooling functionality. Specifically, the tissue ablation system 200 comprises the previously described RF generator 104, a surface electrode 202 additionally configured to cool the target tissue while it is being ablated, and a pump assembly 204 configured for delivering a cooling medium to the surface electrode 102.

Figure 15:
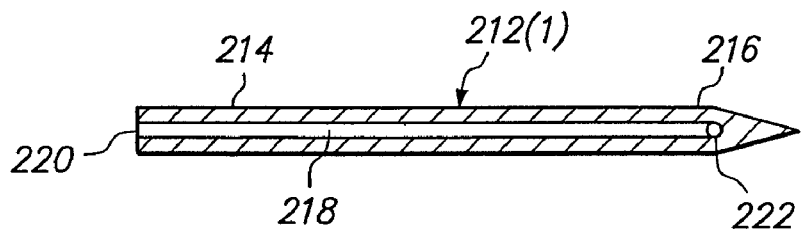
FIG. 15 is a cross-sectional view of one preferred embodiment of a needle electrode that can be used in the tissue ablation system of FIG. 14.
Figure 16:
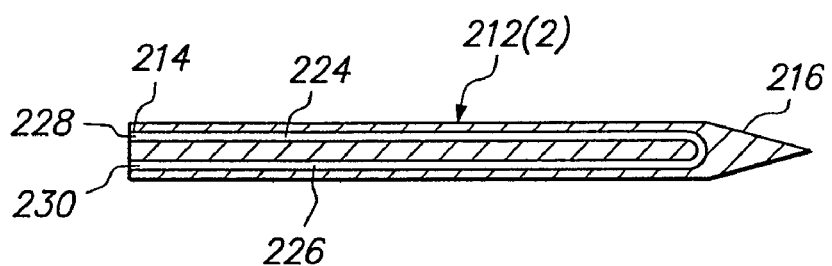
FIG. 16 is a cross-sectional view of another preferred embodiment of a needle electrode that can be used in the tissue ablation system of FIG. 14.

The surface electrode 202 is similar to the surface electrode 102 illustrated in FIG. 5, with the exception that it has cooling functionality. Specifically, the surface electrode 202 comprises needle electrodes 212 that comprise cooling lumens through which a cooling medium can be pumped. In the illustrated embodiment, two types of needle electrodes 212 are used: an irrigated needle electrode 212(1) and an internally cooled needle electrode 212(2). As illustrated in FIG. 15, the irrigated needle electrode 212(1) comprises a cooling lumen 218 that originates at an entry port 220 at the proximal end 214 of the needle electrode 212(1) and terminates at an exit port 222 at the distal end 216 of the needle electrode 212(1). As a result, a cooling medium that is conveyed through the entry port 220 and distally through the cooling lumen 218 is perfused out from the exit port 222 into the surrounding tissue, thereby cooling the tissue while it is being ablated. As illustrated in FIG. 16, the internally cooled needle electrode 212(2) comprises a cooling lumen 224 that originates at an entry port 228 at the proximal end 214 of the needle electrode 212(2) and a return lumen 226 that terminates at an exit port 230 at the proximal end 214 of the needle electrode 212(2). The cooling and return lumens 224 and 226 are in fluid communication with each other at the distal end 216 of the needle electrode 212(2). As a result, a cooling medium is conveyed into the entry port 228 and distally through the cooling lumen 224 to cool the shaft of the needle electrode 212(2), with the resultant heated medium being proximally conveyed through the return lumen 226 and out through the exit port 230. It should be noted that for the purposes of this specification, a cooling medium is any medium that has a temperature suitable for drawing heat away from the surface electrode 202. For example, a cooling medium at room temperature or lower is well suited for cooling the surface electrode 202.

Figure 17:
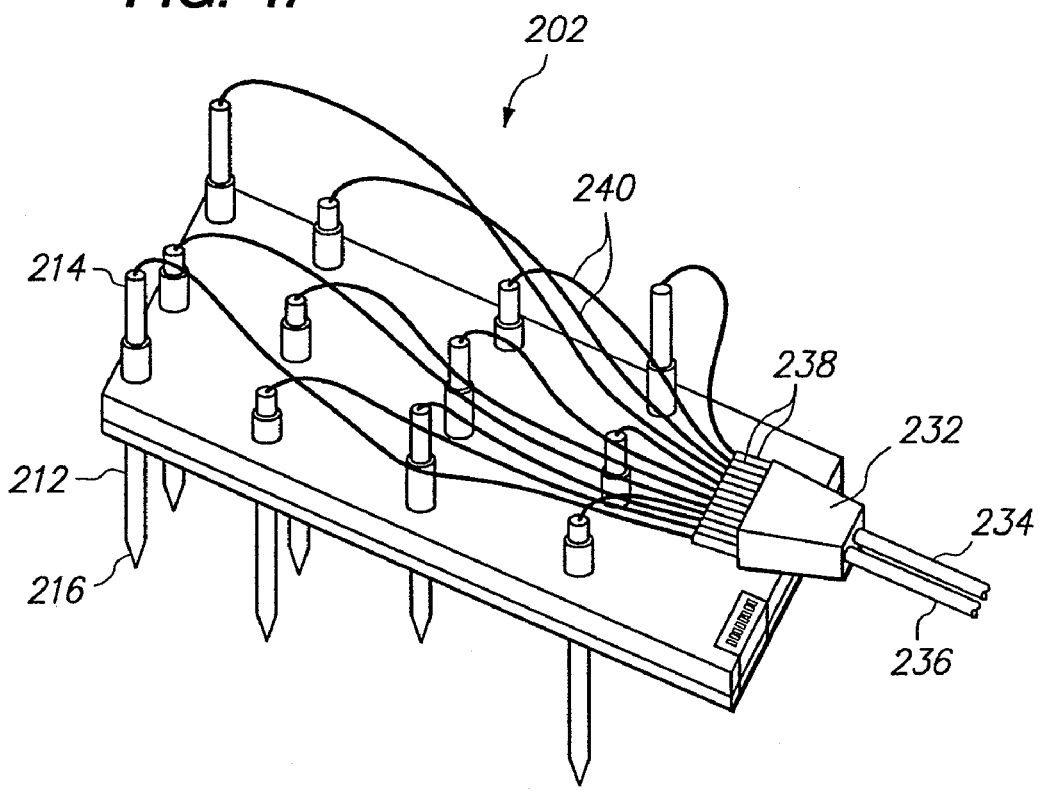
FIG. 17 is a perspective view of a preferred embodiment of a surface electrode that can be used in the tissue ablation system of FIG. 15.

Referring to FIG. 17, the surface electrode 202 further comprises a fluid manifold 232 having an inlet fluid port 234 and an outlet fluid port 236 that are configured to be connected to the pump assembly 204, as will be described in further detail below. The fluid manifold 232 further comprises an array of branch ports 238 that are in fluid communication with the inlet and outlet ports 234 and 236.

The surface electrode 202 further comprises an array of conduits 240 that are respectively mounted at their proximal ends to the branched ports 238 of the cooling manifold 232 and at their distal ends to proximal ends 214 of the needle electrodes 212 in fluid communication with the lumens therein. The conduits 240 that are associated with the irrigated needle electrodes 212(1) each comprises a single cooling lumen (not shown) that is in fluid communication between the inlet port 234 of the cooling manifold 232 and the entry port 220 (shown in FIG. 15) of the respective needle electrode 212(1). The conduits 240 that are associated with the internally cooled needle electrodes 212(2) each comprises a cooling lumen (not shown) that is in fluid communication between the inlet port 234 of the cooling manifold 232 and the entry port 228 (shown in FIG. 16) of the respective needle electrode 212(2), and a return lumen (not shown) that is in fluid communication between the outlet port 236 of the cooling manifold 232 and the exit port 230 (shown in FIG. 16) of the respective needle electrode 212(2).

Referring back to FIG. 14, the pump assembly 204 comprises a power head 242 and a syringe 244 that is front-loaded on the power head 242 and is of a suitable size, e.g., 200 ml. The power head 242 and the syringe 244 are conventional and can be of the type described in U.S. Pat. No. 5,279,569 and supplied by Liebel-Flarsheim Company of Cincinnati, Ohio. The pump assembly 204 further comprises a source reservoir 246 for supplying the cooling medium to the syringe 244, and a discharge reservoir 248 for collecting the heated medium from the surface electrode 202. The pump assembly 204 further comprises a tube set 250 removably secured to an outlet 252 of the syringe 244. Specifically, a dual check valve 254 is provided with first and second legs 256 and 258. The first leg 256 serves as a liquid inlet connected by tubing 260 to the source reservoir 246. The second leg 258 serves as a liquid outlet and is connected by tubing 262 to the inlet fluid port 234 on the cooling manifold 232 of the surface electrode 202. The discharge reservoir 248 is connected to the outlet fluid port 236 on the cooling manifold 232 of the surface electrode 202 via tubing 264.

Thus, it can be appreciated that the pump assembly 204 can be operated to periodically fill the syringe 244 with the cooling medium from the source reservoir 246, and convey the cooling medium from the syringe 244, through the tubing 262, and into the inlet fluid port 232 on the cooling manifold 232. The cooling medium will then be conveyed through the branched ports 238 of the cooling manifold 232, through the cooling lumens on the conduits 240 (shown in FIG. 17), and into the cooling lumens 218 and 224 in the respective needle electrodes 212(1) and 212(2) (shown in FIGS. 15 and 16). With respect to the irrigated needle electrodes 212(1), the cooling medium will be perfused into the tissue to cool it. With respect to the internally cooled needle electrodes 212(2), the cooling medium will be internally circulated within the needle electrode 112 to cool it. The resultant heated medium will be conveyed from the return lumens 226 of the needle electrodes 212(2), through the return lumens of the conduits 240, and into the branched ports 238 of the cooling manifold 232. The heat medium will then be conveyed from the outlet fluid port 234 on the cooling manifold 232, through the tubing 264, and into the discharge reservoir 248.

Operation of the tissue ablation system 200 will be similar to that of the tissue ablation system 100, with the exception that the pump assembly 204 will be operated to cool the target tissue and needle electrodes 212. Optionally, the cooling medium can contain a therapeutic agent that can be delivered to the tissue via the irrigated needle electrodes 212(2). The pump assembly 204, along with the RF generator 104, can include control circuitry to automate or semi-automate the cooled ablation process.

Figure 18:
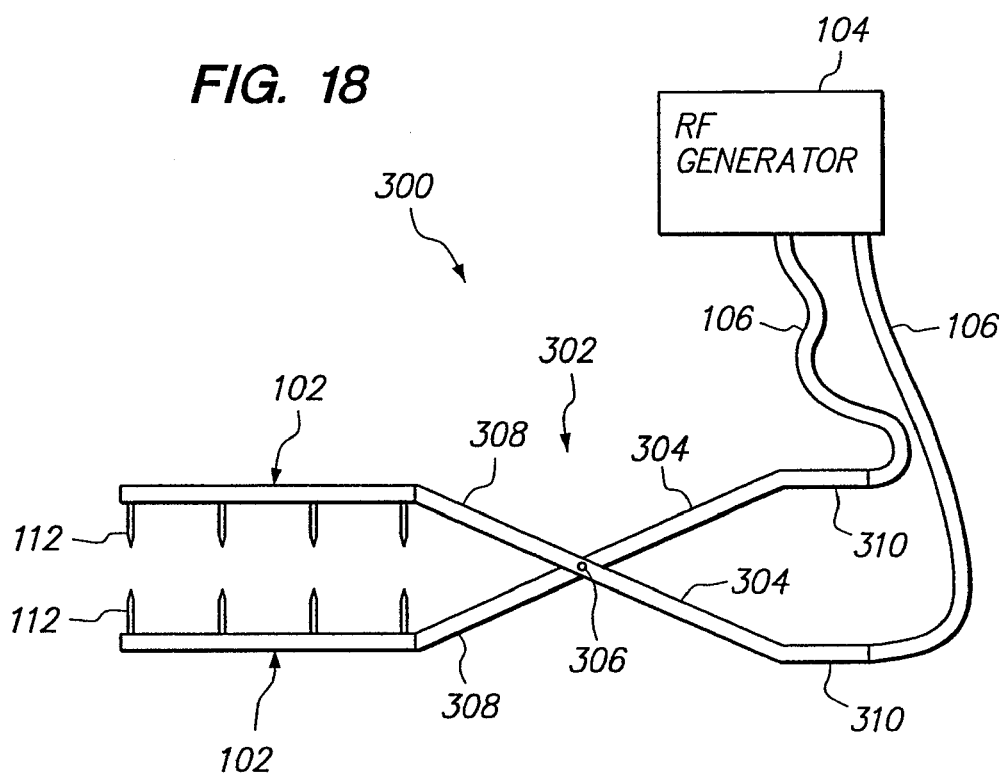
FIG. 18 is plan view of a tissue ablation system constructed in accordance with still another preferred embodiment of the present inventions.

FIG. 18 illustrates a tissue ablation system 300 constructed in accordance with still another preferred embodiment of the present invention. The tissue ablation system 300 is similar to the previously described tissue ablation system 100, with the exception that it comprises an ablative clamping device 302 that incorporates two surface electrodes 102. In particular, the clamping device 302 comprises two opposing clamping members 304 that are coupled to each other via a pivot point 306. The surface electrodes 102 are mounted to arms 308 of the respective clamping members 304, such that the needle electrodes 112 of the surface electrodes 102 oppose each other. The clamping members 304 include handles 310 that, when closed, move the opposing needles 112 of the respective surface electrodes 102 away from each other, and when opened, move the opposing needles 112 of the respective surface electrodes 102 towards each other. Thus, it can be appreciated that the clamping device 302 can engage and penetrate tissue in an opposing manner when the handles 310 of the clamping device 302 are opened, and disengage the tissue when the handles 310 are closed.

The cables 106 of the RF generator 104 are coupled to the electrical interfaces (not shown in FIG. 18) of the respective surface electrodes 102 via RF wires (not shown) extending through the clamping members 304. In the illustrated embodiment, the respective surface electrodes 102 are coupled to the RF generator 104 in a bipolar arrangement, i.e., one surface electrode 102 is coupled to the first pole of the RF generator 104, and the other surface electrode 102 is coupled to the second pole of the RF generator 104. The needle electrodes 112 on each of the surface electrodes 102 can be selectively activated using the electrical interface on the respective surface electrode 102. Alternatively, only one of the surface electrodes 102 is activated, in which case, the other surface electrode merely serves as a means for stabilizing the other surface electrode 102 within the tissue. The needle electrodes 112 of the active surface electrode 102 can be designed to be placed in a bipolar arrangement or a monopolar arrangement. Deactivation of the surface electrode 102 can be accomplished via the electrical interface, or alternatively, a stabilizing member with non-active needles, or a stabilizing member with no tissue penetrating needles, can be used instead of a potentially active surface electrode 102.

Figure 19:
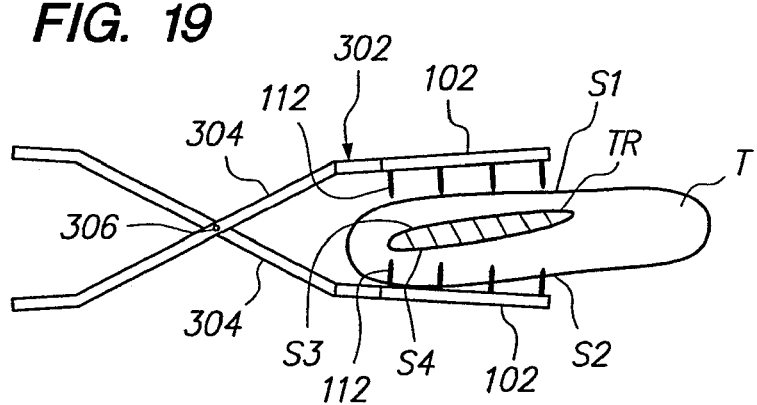
FIGS. 19-20 are plan views illustrating one preferred method of using the tissue ablation system of FIG. 18 to ablate a treatment region within tissue of a patient.
Figure 20:
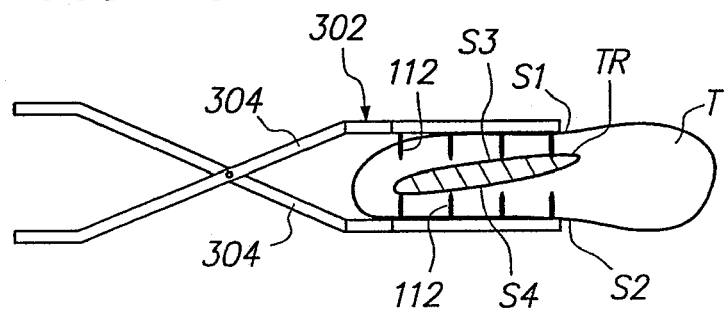

Referring now to FIGS. 19 and 20, operation of the tissue ablation system 300 is described in treating a treatment region TR, such as a tumor, located between opposing surfaces S1 and S2 of tissue T, e.g., an organ. The treatment region TR also has opposing surfaces S3 and S4.

First, the electrical interface(s) on the surface electrodes 102 are configured, based on the shape of the treatment region TR and whether a monopolar or a bipolar arrangement is desired. The surface electrodes 102 are then positioned, such that they are respectively adjacent the opposing surfaces S1 and S2 of the tissue T, as illustrated in FIG. 19. Preferably, access to the tissue T is gained through a surgical opening made through the skin of the patient. The clamping device 302 can be closed, while introduced through the opening, and then opened in order to place the tissue T between the opposing surface electrodes 102. Alternatively, each individual clamping member 304 and associated surface electrode 102 can be introduced through two respective laparoscopes and then subsequently assembled at the pivot point 306.

Next, the clamping device 302 is closed, such that the needle electrodes 112 of the respective surface electrodes 102 penetrate through the surfaces S1 and S2 into the tissue T, as illustrated in FIG. 20. As illustrated, the application of pressure by the clamping device 302, causes the tissue T in contact with the surface electrodes 102 to compress. Once the needle electrodes 112 are embedded into the tissue T, the distances that the needle electrodes 112 extend from the base 108 of the surface electrode 102 are individually adjusted in the manner previously described. If provided, the optional insulating sleeves can also be adjusted. The RF generator 104 is then connected to the clamping device 300, and then operated to ablate the treatment region TR, resulting in the formation of a lesion that preferably encompasses the entirety of the treatment region TR. If the treatment region TR is substantially larger than that which the surface electrode 102 can cover, thereby resulting in a treatment region TR that is only partially ablated, the clamping device 302 can be opened to release the needle electrodes 102 from the tissue T, and then reapplied to a different portion of the tissue T.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A surface electrode for ablating tissue, comprising:
a base having a surface;
a plurality of apertures in the base, each aperture including a screw threaded inner surface;
a plurality of tissue penetrating needle electrodes extending from the surface of the base an adjustable distance, wherein the needle electrodes have screw threaded outer surfaces that respectively cooperate with the screw threaded inner surfaces of the apertures, such that rotation of each needle electrode in one direction increases the distance that the needle electrode extends from the surface of the base, and rotation of each needle electrode in another direction decreases the distance that the needle electrode extends from the surface of the base;
a plurality of electrical paths coupled to the electrodes via the apertures; and
an electrical interface coupled to the electrical paths.

2. The surface electrode of claim 1, wherein the electrical paths comprise electrical traces that extend along the base.

3. The surface electrode of claim 1, wherein the base comprises a plate from which the plurality of needle electrodes extends.

4. The surface electrode of claim 1, wherein the surface of the base is flat.

5. The surface electrode of claim 1, wherein the surface of the base is electrically insulated.

6. The surface electrode of claim 1, wherein the surface of the base is electrically conductive.

7. The surface electrode of claim 1, wherein distances at which the needle electrodes extend from the surface of the base are individually adjustable.

8. The surface electrode of claim 1, wherein the electrical interface couples at least some of the needle electrodes in a bipolar arrangement with respect to each other.

9. The surface electrode of claim 1, wherein the electrical interface is adjustable, so that certain needle electrodes can be selectively activated.

10. The surface electrode of claim 1, wherein one or more of the plurality of needle electrodes comprises a liquid conveying lumen.

11. The surface electrode of claim 10, wherein at least one of the lumens is configured to perfuse a medium from the respective needle electrodes, and at least another of the lumens is configured to internally convey a medium within the respective needle electrodes.

12. A system for ablating tissue, comprising:
a surface electrode including a base having a surface, a plurality of apertures in the base, each aperture including a screw threaded inner surface, a plurality of tissue penetrating needle electrodes extending from the surface of the base an adjustable distance, wherein the needle electrodes have screw threaded outer surfaces that respectively cooperate with the screw threaded inner surfaces of the apertures, such that rotation of each needle electrode in one direction increases the distance that the needle electrode extends from the surface of the base, and rotation of each needle electrode in another direction decreases the distance that the needle electrode extends from the surface of the base, a plurality of electrical paths coupled to the electrodes via the apertures, and an electrical interface coupled to the electrical paths; and
an ablation source coupled to the electrical interface.

13. The system of claim 12, wherein the electrical paths comprise electrical traces that extend along the base.

14. The system of claim 12, wherein the base comprises a plate from which the plurality of needle electrodes extends.

15. The system of claim 12, wherein the surface of the base is flat.

16. The system of claim 12, wherein the surface of the base is electrically insulated.

17. The system of claim 12, wherein the surface of the base is electrically conductive.

18. The system of claim 12, wherein distances at which the needle electrodes extend from the surface of the base are individually adjustable.

19. The system of claim 12, wherein the electrical interface couples at least some of the needle electrodes in a bipolar arrangement with respect to each other.

20. The system of claim 12, wherein the electrical interface is adjustable, so that certain needle electrodes can be selectively activated.

21. The system of claim 12, wherein one or more of the plurality of needle electrodes comprises a lumen, the system further comprising a source of cooling medium in communication with the lumen.

22. The system of claim 21, wherein at least one of the lumens is configured to perfuse a medium from the respective needle electrodes, and at least another of the lumens is configured to internally convey a medium within the respective needle electrodes.

23. The system of claim 12, wherein the ablation source comprises a radio frequency (RF) generator.

24. An ablative clamping device, comprising:
first and second opposing arms; and
a stabilizing member, wherein the surface electrode of claim 1 is mounted on the first arm, and the stabilizing member is mounted to the second arm.

* * * * *